Figure 1:
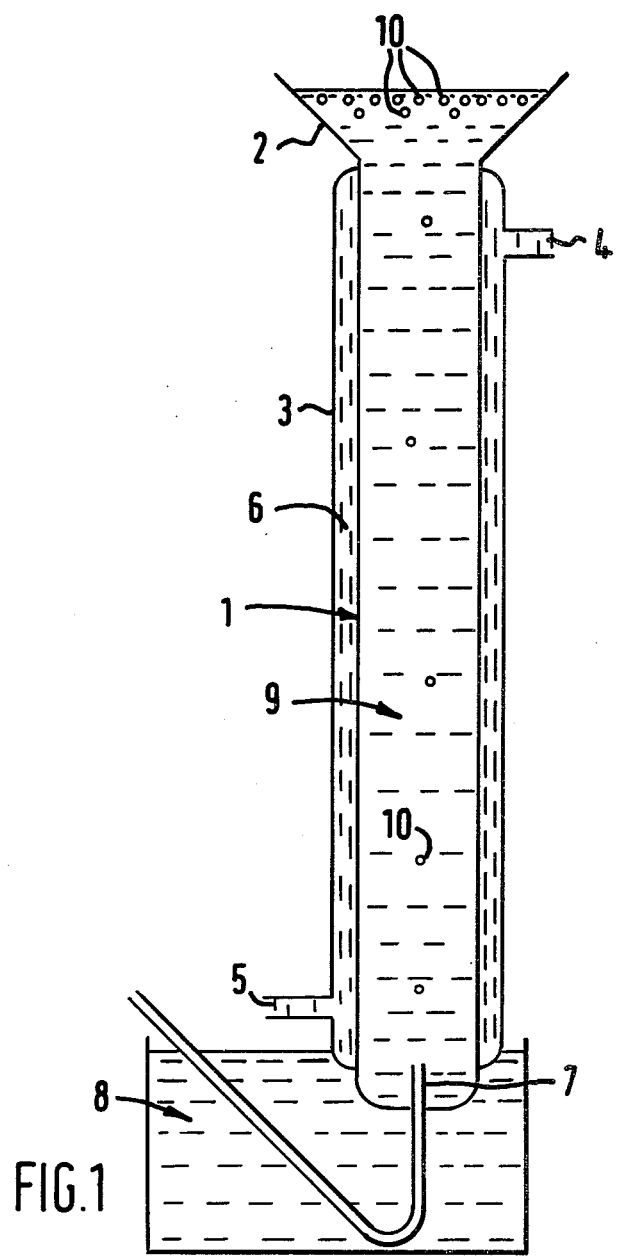

United States Patent [19]

Buxton et al.

[11] Patent Number: 4,470,202
[45] Date of Patent: Sep. 11, 1984

[54] PROCESS AND APPARATUS FOR FREEZING A LIQUID MEDIUM

[75] Inventors: Ian R. Buxton; James M. Peach, both of High Wycombe, England

[73] Assignee: John Weyeth & Brother Limited, Maidenhead, England

[21] Appl. No.: 444,652

[22] Filed: Nov. 26, 1982

[30] Foreign Application Priority Data

Dec. 11, 1981 [GB] United Kingdom ............. 81 37526

[51] Int. Cl.³ .......................... F26B 5/06; B01D 9/04
[52] U.S. Cl. .......................................... 34/5; 62/123
[58] Field of Search .................. 34/5, 9; 62/74, 123

[56] References Cited

U.S. PATENT DOCUMENTS

| | | | |
|---|---|---|---|
| 2,751,762 | 6/1956 | Colton | 62/173 |
| 3,484,946 | 12/1969 | Saver | 62/123 |
| 3,653,222 | 4/1972 | Dunn et al. | 62/74 |
| 3,655,838 | 4/1972 | Price et al. | 264/13 |
| 3,959,513 | 5/1976 | Strohbach et al. | 62/74 |

FOREIGN PATENT DOCUMENTS

| | | |
|---|---|---|
| 178013 | 9/1935 | Switzerland . |
| 764718 | 1/1957 | United Kingdom . |
| 927218 | 5/1963 | United Kingdom . |
| 1251526 | 10/1971 | United Kingdom . |
| 1316522 | 5/1973 | United Kingdom . |
| 1320467 | 6/1973 | United Kingdom . |
| 1340015 | 12/1973 | United Kingdom . |
| 1548022 | 7/1979 | United Kingdom . |
| 1549471 | 7/1981 | United Kingdom . |

*Primary Examiner*—John J. Camby
*Attorney, Agent, or Firm*—Arthur E. Wilfond

[57] ABSTRACT

Spherical frozen particles, which may be subsequently freeze dried are prepared by introducing a liquid medium in the form of droplets beneath the surface of a cooling liquid. The temperature and density of the cooling liquid is chosen so that liquid droplets freeze as they float towards the surface of the cooling liquid. Preferably a column of cooling liquid is employed and the liquid medium is introduced through an inlet near the base of the column.

11 Claims, 2 Drawing Figures

PROCESS AND APPARATUS FOR FREEZING A LIQUID MEDIUM

This invention relates to a process and apparatus for freezing a liquid medium, in particular to a process and apparatus for freezing a liquid medium to give spherical frozen particles.

Freeze drying of liquid mediums, e.g. liquid solutions or suspensions, normally involves freezing the medium and then subsequently subliming the liquid from the frozen material in, for example, a vacuum chamber (freeze drier), to give the freeze dried product. Many methods of freezing are known. For example the liquid medium can be contained in a mould or other container which is cooled with solid carbon dioxide, liquid nitrogen or the like. In an alternative method the mould or other container containing the liquid medium may be passed through a freezing tunnel into which liquid nitrogen is injected, the nitrogen being vapourised and the resulting cold gaseous nitrogen being passed over the liquid medium. In these prior art methods of freezing the liquid is frozen in a container which is wasteful of space both in the freezing apparatus and also in any subsequent processing apparatus such as the freeze drier. In contrast the present invention relates to a process for freezing a liquid medium to given spherical particles of frozen material. These spherical particles may be handled in bulk making the subsequent processing more economical by, for example, saving space in the freeze drier.

According to the present invention there is provided a process for freezing a liquid medium to produce spherical frozen particles which process comprises introducing the liquid medium in the form of droplets beneath the surface of a cooling liquid which is maintained at a temperature lower than the freezing point of the liquid medium, the cooling liquid being immiscible with, and inert with respect to, the liquid medium and having a density greater than that of both the liquid medium and the resulting frozen particles such that as the liquid droplets float upwards in the cooling liquid towards the surface thereof, they are frozen to form spherical particles. Preferably the frozen spherical particles are collected at or near the upper surface of the cooling liquid. The frozen spherical particles are of substantially uniform size and constitution.

The process of the invention is particularly suitable for freezing aqueous solutions or suspensions, especially such solutions or suspensions which require to be subsequently freeze dried. U.S. Pat. Nos. 4,305,502 and 4,371,516 claim priority from the same U.K. applications as French Pat. No. 2,366,835, and which issued as U.K. Pat. No. 1,548,022. These patents disclose a method of producing shaped articles which are rapidly disintegratable by water and which carry predetermined unit quantities of chemicals by a process involving sublimation of a solvent from a frozen composition comprising the predetermined amount of chemical and a solution in a solvent (especially an aqueous solvent) of a water soluble or water dispersible carrier material so as to give a network of carrier material carrying the chemical. Our copending application entitled "Solid Shaped Articles" (Ser. No. 445,138) which is being filed concurrently herewith and which claims priority from UK Patent Application No. 8137525 discloses the preparation of similar solid shaped articles by a process involving sublimation of a solvent from a frozen composition comprising a solution in a solvent of a carrier material and then subsequently dosing the predetermined amount of chemical on to the freeze dried article. The process of the present invention is particularly useful for freezing compositions comprising a solution in an aqueous solvent of a carrier material which upon subsequent freeze drying forms a network which is rapidly disintegratable in water (for example within 5 seconds at 20° C.) The compositions may contain a predetermined amount of a chemical such as a pharmaceutical substance and the resulting frozen spherical particles may be freeze dried. If the composition contains a unit dose of chemical then a single freeze dried sphere may constitute a unit dosage which may be administered, dispensed or otherwise utilised in applications where it is desired to employ chemicals (such as pharmaceuticals) in predetermined unit quantities. Alternatively the composition which is frozen may contain less than the unit dosage of chemical and a number of freeze dried spheres would then constitute a unit dosage of chemical. The requisite number of freeze dried spheres can, if desired, be packeted together (e.g. in a sachet or the like) to provide a unit dosage. In an alternative embodiment the composition containing the carrier material without the chemical may be frozen and the frozen spherical particles freeze dried. The chemical may then be dosed on to the resulting freeze dried spheres. This embodiment is particularly advantageous if the amount of chemical to be carried by each sphere is not especially critical (for example in non-pharmaceutical uses, e.g. confectionary). In such applications the chemical may, for example, be sprayed on to the freeze dried spheres.

Examples of suitable carrier materials, particularly those that are pharmaceutically acceptable for use in preparing pharmaceutical dosage forms are given in the above mentioned specifications. For example, the carrier may be formed from polypeptides such as gelatin, particularly gelatin which is partially hydrolysed, e.g. by heating in water. For example, the gelatin may be partially hydrolysed by heating a solution of the gelatin in water, e.g. in an autoclave at about 120° C. for up to 2 hours, e.g. from about 5 minutes to about 1 hour, preferably from about 30 minutes to about 1 hour. The hydrolysed gelatin is preferably used at concentrations of about 1 to 6% weight/vol., most preferably at 2 to 4% e.g. about 3%. Other carrier materials may be used in place of partially hydrolysed gelatin for example polysaccharides such as dextran (in particular dextran of average molecular weight from 60,000 to 275,000 e.g. 150,000 to 200,000), dextrin and alginates (e.g. sodium alginate) or mixtures of above mentioned carriers with each other or with other carrier materials such as polyvinyl alcohol, polyvinylpyrrolidine or acacia. The dextran is preferably used at a concentration of about 4% to 20% weight/volume, e.g. about 6% to 18% (if the mol. weight is 150,000 to 200,000) or about 6% to 10% (if the mol. weight is 200,000 to 275,000).

Besides the chemical and the carrier material the composition to be frozen may contain other additional ingredients. For example, when preparing pharmaceutical dosage forms the composition may include pharmaceutically acceptable adjuvants such as colouring agents, flavouring agents, preservatives and the like. In addition the composition may contain ingredients which aid in the preparation of the shaped articles. For example, the composition may include a surfactant, e.g. Polysorbate 80 BPC [polyoxyethylene (20) sorbitan mono-oleate], to aid in the dispersion of the chemical. The composition may also include ingredients such as fillers (e.g. mannitol, sorbitol) which improve the physical properties of the freeze dried spherical product.

The solvent for the composition is preferably water but it may contain a co-solvent (such as an alcohol) if it is desired to improve the solubility of the chemical.

According to the process of the invention the composition to be frozen is introduced in the form of droplets beneath the surface of a cooling liquid. Preferably a column of cooling liquid is employed and the composition is introduced near the base of the column. The composition is introduced into the cooling liquid as a liquid drop which floats upwards within the cooling liquid. As it rises the composition is gradually frozen so that the frozen spherical particles may be collected at or near the top of the column. The rate of ascent of the drop and the rate of freezing may be varied by using a cooling liquid of a suitable density and viscosity, maintaining the cooling liquid at the required temperature and employing a column of cooling liquid of suitable length. The length of the column may be reduced if the cooling liquid is circulated in a direction opposite to the direction of the ascent of the drop so that the rate of the ascent of the drop is reduced.

The cooling liquid should be immiscible with the liquid medium. If the liquid medium is an aqueous solution or suspension (such as the compositions mentioned above containing a carrier material) the cooling liquid preferably has a density of about 1.05 to 1.4. Preferably the cooling liquid remains liquid to temperatures of at least $-50°$ C. in order to provide for sufficiently rapid freezing of the liquid medium. Suitable cooling liquids include trichloroethane, trichloroethylene, dichloromethane, diethyl ether and fluorotrichloromethane.

The liquid medium is introduced under the surface of the cooling medium in the form of liquid drops. For example the liquid medium may be introduced into the cooling medium through an orifice of a size to provide drops of the required size. The size of the spherical frozen particles is also dependant upon the relative densities of the liquid medium and the cooling liquid. In order to prevent the liquid medium freezing around the orifice, the orifice may be maintained at higher temperature than that of the cooling liquid.

The invention also provides an apparatus for use according to the process of the invention. According to the invention an apparatus for freezing a liquid medium to produce spherical frozen particles comprises a container for a cooling liquid, means for maintaining the temperature of the cooling liquid at a temperature below that of the freezing point of the liquid medium, an inlet in the container for introducing the liquid medium in the form of droplets below the surface of the cooling liquid, means for maintaining the temperature of the inlet above that of the freezing point of the liquid medium and means for collecting the frozen spherical particles at a position nearer the surface than the inlet. It should be understood that the means for collecting the frozen particles does not necessarily have to be positioned vertically above the inlet, provided that the means are nearer the surface of the cooling liquid than the inlet. Preferably the means are positioned at or near the surface of the cooling liquid.

The container for the cooling liquid is preferably a column of sufficient length to contain the requisite amount of cooling liquid. The column can be jacketed and a heat transfer medium may be circulated through the jacket to maintain the cooling liquid at the desired temperature. The inlet may be in the form of a tube or the like of internal diameter of, for example, 0.5 to 5 mm, e.g. 2 mm. The inlet may be maintained at a higher temperature than the cooling liquid by, for use, an electrical heater or by a heat exchange liquid (e.g. a water bath).

Figure 2:
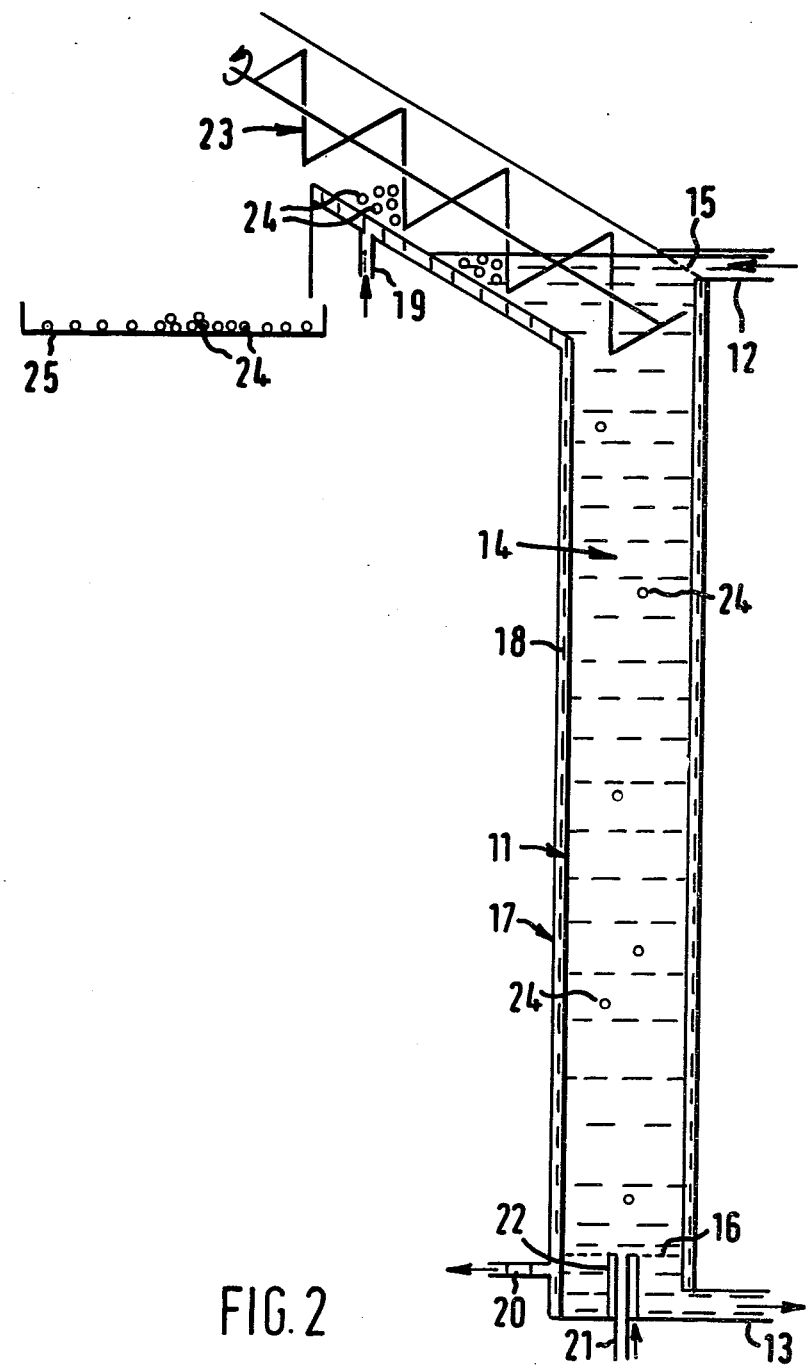

An apparatus in accordance with the invention will now be described with reference to the accompanying drawings in which:

FIG. 1 is a diagrammatic side elevation of a first embodiment of the invention, and FIG. 2 is a diagrammatic side elevation of a second embodiment of the invention.

As shown in FIG. 1, an apparatus for freezing a liquid medium to produce spherical frozen particles comprises a vertical column 1 of about 90 cm in length having a flared upper part 2. Surrounding the column 1 is a jacket 3 having an inlet 4 and an outlet 5. A heat transfer medium 6 is circulated through the jacket and is maintained at a low temperature by passing it through a refrigeration apparatus (not shown).

An inlet pipe 7 enters the column 1 near its base. Part of the inlet tube 7 is immersed in a water bath 8 containing water at room temperature which maintains the inlet tube 7 at the desired temperature.

The column 1 contains cooling liquid 9.

As described in greater detail below, the liquid medium to be frozen may be introduced from the inlet pipe 7 (by means of, for example, a peristaltic pump—not shown) into the cooling liquid 9. Droplets 10 are formed which freeze as they float upwards and the frozen spheres collect in the flared portion 2, from which they may be removed. After removal they may be kept in a cold store or freeze dried.

In the embodiment shown in FIG. 2, the vertical column 11 has an inlet 12 near the top and an outlet 13 near the base so that the cooling liquid 14 circulates in the direction shown by the arrows. The inlet 12 and outlet 13 are protected by filters 15, 16 which allow circulation of the cooling liquid but prevent passage of the spherical particles. Surrounding the column 11 is a jacket 17 through which the heat transfer medium 18 is circulated through an inlet 19 and out through the outlet 20. The heat transfer medium is maintained at a low temperature by passing it through a refrigeration apparatus (not shown).

An inlet pipe 21 for the liquid medium enters the column 11 near its base. The open end of the pipe 21 is surrounded by an electrically heated collar 22.

In the open top of the column 11 there is situated a worm mechanism 23 designed to be driven at about 10 r.p.m. Droplets of liquid medium entering the cooling liquid 14 through the inlet 21 become frozen as they float upwards in the cooling medium and the resulting spherical frozen particles 24 are removed from the top surface of the cooling liquid by the worm mechanism 23. The spheres are dropped by the worm mechanism into a tray 25 in which they may be transported to a cold store or direct to the freeze drier.

The following Examples illustrate the process of the invention:

EXAMPLE 1

A 3% w/v hydrolysed gelatin solution is prepared by dissolving 30 g of gelatin B.P. in water (made up to 1000 ml) with heat and constant stirring and autoclaving at 121° C. for 60 minutes. After allowing to cool, 30 g of oxazepam and 30 g mannitol is added to form a suspension which is injected by means of a peristaltic pump at a rate of about 5 ml per minute into a cooling liquid using the embodiment shown in FIG. 1. The cooling liquid is dichloromethane maintained at a temperature of about −30° C. using trichloroethylene as the heat transfer medium in the jacket. The trichloroethylene is admitted into the top of the jacket at about −40° C. and exhausted from the bottom. The trichloroethylene is then pumped through a heat exchange coil immersed in a mixture of alcohol and solid carbon dioxide at a temperature of −78° C. and returned to the top of the jacket.

The oxazepam/mannitol/hydrolysed gelatin suspension is pumped into the cooling liquid through a narrow steel tube of about 2.0 mm internal diameter. The base of the column is immersed in a cold water bath to above the level of the steel tube.

As the pump injects the suspension into the cooling liquid droplets rise through the cooling liquid and freeze to form spherical particles which collect in the flared top of the column.

The frozen spheres are removed from the column, drained and freeze dried in a freeze drier at a pressure of 0.4 mm Hg and a temperature of 60° C. for 2 hours.

The resulting freeze dried spheres constitute a pharmaceutical dosage form which dissolve rapidly in water (within 5 secs. at 20° C.) and also in the mouth (within 2 seconds). Sixteen of the spheres, each of diameter about 2 to 3 mm constitute a 15 mg dose of oxazepam.

EXAMPLE 2

The procedure of Example 1 is followed replacing the 3% oxazepam by 3.2% lorazepam, to give freeze dried spheres, each of which constitutes a single dose of 1 mg lorazepam.

EXAMPLE 3

The procedure of Example 1 is followed replacing the 3% oxazepam by 0.7% cyclopenthiazide to give freeze dried spheres, each of which contains 0.25 mg cyclopenthiazide.

The oxazepam may be replaced by other pharmaceutical substances in particular those disclosed in the above mentioned specifications.

|  | w/w |
| --- | --- |
| Aluminium Hydroxide High Strength Gel (13%) | 15% |
| Dextran (mw 200,000–275,000) | 10% |
| Mannitol B.P. | 3% |
| Peppermint Flavour | 0.3% |
| Thaumatin | 0.002% |
| Sodium Saccharin | 0.02% |
| Water | to 100% |

The above ingredients are mixed thoroughly and pumped at 5 ml/min through a 2 mm orifice into dichloromethane at −15° C. to −20° C. following the procedure of Example 1. The frozen spheres are recovered from the surface of the solvent and freeze dried in beds up to 2 cm deep. Each sphere contains 5 mg of dried Aluminium Hydroxide Gel and weighs 9 mg. 100 spheres constitute a single dose containing 500 mg dried Aluminium Hydroxide Gel. The spheres constituting a unit dose are dispersed in water by the patient prior to taking.

EXAMPLE 5

The procedure of Example 1 is followed replacing the 3% oxazepam by 2.8% indole acetic acid to give spheres each of which contains 1 mg indole acetic acid. The user can dissolve a sphere in a liter of water to give a composition which can be used as a plant growth promoter.

We claim:

1. A process for freezing a liquid medium to produce spherical frozen particles which process comprises introducing the liquid medium in the form of droplets beneath the surface of a cooling liquid which is maintained at a temperature lower than the freezing point of the liquid medium, the cooling liquid being immiscible with, and inert with respect to, the liquid medium and having a density greater than that of both the liquid medium and the resulting frozen particles such that as the liquid droplets float upwards in the cooling liquid towards the surface thereof, they are frozen to form spherical particles and moving the cooling liquid in a direction opposite to that of the ascent of the droplets.

2. A process as claimed in claim 1 in which the frozen spherical particles are collected at or near the upper surface of the cooling liquid.

3. A process as claimed in claim 1 wherein the liquid medium is a composition comprising a solution in an aqueous solvent of a carrier material which upon subsequent freeze drying forms a network which is disintegratable in water.

4. A process as claimed in claim 3 wherein the composition additionally contains a predetermined amount of chemical.

5. A process as claimed in claim 4 wherein the chemical is a pharmaceutical.

6. A process as claimed in claim 5 wherein the carrier material is partially hydrolysed gelatin or dextran.

7. A process as claimed in any one of claims 4 to 6 wherein the cooling liquid is trichloroethane, trichloroethylene, dichloromethane, diethyl ether or fluorotrichloromethane.

8. A process as claimed in any one of claim 1 to 3 wherein the resulting spherical particles are freeze dried.

9. An apparatus for freezing a liquid medium to produce spherical frozen particles comprises a container a cooling liquid, means for maintaining the temperature of the cooling liquid at a temperature below that of the freezing point of the liquid medium, an inlet in the container for introducing the liquid medium in the form of droplets below the surface of the cooling liquid, means for maintaining the temperature of the inlet above that of the freezing point of the liquid medium, means for moving the cooling liquid in a downwardly direction in the container towards the inlet and means for collecting the frozen spherical particles at a position nearer the surface than the inlet.

10. An apparatus as claimed in claim 9 wherein the container for cooling liquid is a column of sufficient length to contain the requisite amount of cooling liquid.

11. An apparatus as claimed in claim 9 or 10 wherein the means for maintaining the inlet at the required temperature comprises an electrical heater or a heat exchange liquid.

* * * * *